United States Patent [19]

Harirchian et al.

[11] Patent Number: 5,320,775

[45] Date of Patent: Jun. 14, 1994

[54] BLEACH PRECURSORS WITH NOVEL LEAVING GROUPS

[75] Inventors: Bijan Harirchian, South Orange; Robert W. R. Humphreys, Oradell, both of N.J.

[73] Assignee: Lever Brothers Company, Division of Conopco, Inc., New York, N.Y.

[21] Appl. No.: 713,242

[22] Filed: Jun. 7, 1991

[51] Int. Cl.$^5$ .............................................. C09K 3/00
[52] U.S. Cl. .................. 252/186.38; 252/95; 252/99
[58] Field of Search ............. 252/186.29, 186.42, 252/186.43, 186.38

[56] References Cited

U.S. PATENT DOCUMENTS 4,128,494 12/1978 Schirmann ............... 252/186.38
4,283,301 8/1981 Diehl ....................... 252/186.38

FOREIGN PATENT DOCUMENTS 2014405 4/1970 France.

OTHER PUBLICATIONS

Chemical Abstracts, vol. 112, No. 23, Jun. 4, 1990, Abstract No. 216193u.
Chemical Abstracts, vol. 108, No. 15, Apr. 11, 1988, Abstract No. 130992j.
Chemical Abstracts, vol. 103, No. 21, Nov. 25, 1985, Abstract No. 177948m.
Chemical Abstracts, vol. 108, No. 13, Mar. 28, 1988, Abstract No. 111789g.
Chemical Abstracts, vol. 95, No. 5, Aug. 3, 1981, Abstract No. 42576j.
Chemical Abstracts, vol. 93, No. 11, Sep. 15, 1980, Abstract No. 113914q.
Chemical Abstracts, vol. 93, No. 11, Sep. 15, 1980, Abstract No. 113904m.
Chemical Abstracts, vol. 88, No. 15, Apr. 10, 1978, Abstract No. 104729c.
Chemical Abstracts, vol. 116, No. 21, May 5, 1992, Abstract No. 213975x.
Journal of the American Chemical Society, 87, pp. 3855-3861, Sep. 5, 1965, "Kinetic Demonstration of a Tetrahedral Intermediate in the Hydrolysis of Diethyl Acetylmalonate and Diethyl Acetylethylmalonate", by Gustav E. Lienhard and William P. Jencks.

*Primary Examiner*—Richard D. Lovering
*Assistant Examiner*—Joseph D. Anthony
*Attorney, Agent, or Firm*—Milton L. Honig

[57] ABSTRACT

A class of malonates having the structures:

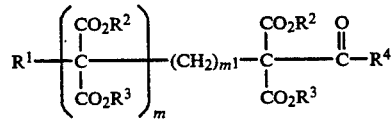

has been identified as providing effective bleach precursors. These precursors are employed in conjunction with a peroxygen compound.

8 Claims, No Drawings

BLEACH PRECURSORS WITH NOVEL LEAVING GROUPS

BACKGROUND OF THE INVENTION

1. Field of the Invention

The invention relates to novel bleach precursors, detergent compositions containing these precursors and methods for removing stains using these compositions.

2. Related Art

It is well-known that active oxygen-releasing compounds are effective bleaching agents. These compounds are frequently incorporated into detergent compositions for stain and soil removal. Unlike the traditional sodium hypochlorite bleaches, oxygen-releasing compounds are less aggressive and thus more compatible with detergent formulations. There is, however, an important limitation to these bleaches; activity is extremely temperature dependent. Thus, oxygen-releasing bleaches are essentially only practical when the bleaching solution is heated above 60° C.. At a temperature of just 60° C., extremely high amounts of the active oxygen-releasing compounds must be added to the system to achieve any bleach effect. Although this would indicate the desirability of high temperature operation, high temperatures are both economically and practically disadvantageous.

At bleach solution temperatures below 60° C., the active oxygen-releasing compounds are rendered much less effective regardless of their level in the system. With respect to bleaching of laundry in automatic household washing machines, it must be noted that these machines are normally operated at wash-water temperatures below 60° C. Consequently, there has developed a need for substances which promote release of active oxygen at temperatures below 60° C. These substances are generally referred to in the art as bleach precursors, although they have also been called promotors and activators. Normally, bleach precursors are used in conjunction with persalts capable of releasing hydrogen peroxide in aqueous solution, perborate being the most widely used persalt.

Typically, the precursor is a reactive compound such as a carboxylic acid ester that in alkaline detergent solution containing a source of hydrogen peroxide, e.g. a persalt, will generate the corresponding peroxy acid derivative. The reaction involves nucleophilic substitution onto the precursor by hydroperoxyl anions (HOO—) and is facilitated by precursors having good leaving groups. Often the reaction is referred to as a perhydrolysis.

Early patents in the area of precursor chemistry include U.S. Pat. No. 3,256,198 (Matzner) and U.S. Pat. No. 3,272,750 (Chase) each of which suggest the use of organic carbonate esters as bleach aids. Unfortunately, some of the better bleaching esters were later found to have a malodor problem.

British Patent 836,988 (Davies et. al.) and British Patent 864,798 (Hampson et. al.) were forerunners disclosing the use of aliphatic carboxylic acid esters as adjuncts for accelerating the bleaching of persalts such as sodium perborate or percarbonate.

U.S. Pat. No. 4,283,301 (Diehl) discloses a peroxygen bleach and a precursor of the general formula:

wherein R is an alkyl chain containing from 5 to 13 carbon atoms, $R^2$ is an alkyl chain containing from 4 to 24 carbon atoms and each Z is a leaving group as defined therein.

U.S. Pat. No. 4,412,934 (Chung et. al.) reports compositions incorporating bleach precursors of the general formula:

wherein R is an alkyl group containing from 5 to 18 carbon atoms and L is a leaving group.

Similar disclosures are found in U.S. Pat. No. 4,486,327 (Murphy et. al.), EP 0 098 129 (Hardy et. al.), EP 0 106 584 (Hartman), EP 0 106 634 (Chung et. al.), EP 0 120 591 (Hardy et. al.), EP 0 163 331 (Burns et. al.), EP 0 166 571 (Hardy et. al.), EP 0 185 522 (Fong et. al.), EP 0 170 386 (Burns et. al.), EP 0 153 222 (Moyne et. al.), EP 0 153 223 (Moyne et. al.) and EP 0 202 698 (Nollet et. al.). Among the preferred leaving groups are those having solubilizing functionality including sulfonic, sulfuric, carboxylate and quaternary ammonium salt groups.

A typical precursor within the concept of the aforedescribed patents is sodium n-nonanoyloxybenzene sulfonate presently commercialized as a component of a branded detergent. This sulfonate, in combination with sodium perborate, effectively releases peroxygen fragments upon perhydrolysis, as well as sodium 4-sulfophenolate. For environmental and other reasons it may be desirable to avoid the use of sulfophenol salts.

While the aforementioned precursors have all been reported effective at stain removal, there is still a need for more efficient systems. Stain removal efficiency may be improved either by a precursor that generates equivalent bleach at a lower precursor molar level or operates at lower levels of hydrogen peroxide source. Not only do lower levels of peroxide source or precursor provide better economics, they also permit increased flexibility in detergent formulation.

Consequently, it is an object of the present invention to provide a detergent-bleach composition with a precursor that permits bleaching over a wide temperature range including that of under 60° C.

Another object of the present invention is to provide certain novel bleach precursors which have hitherto not been described in the art.

A further object of the present invention is to provide bleach precursors which are of pleasant odor.

A still further object of the present invention is to provide a precursor that can be economically synthesized from readily available starting materials and in a minimum number of synthetic steps.

These and other objects of the present invention will become more readily apparent by consideration of the detailed description which follows.

SUMMARY OF THE INVENTION

A bleaching composition is provided comprising:
(i) a peroxygen compound present in an effective amount to generate perhydroxyl anions; and (ii) a bleach precursor present in an effective amount to react with the perhydroxyl anions and cause bleaching, having the structure:

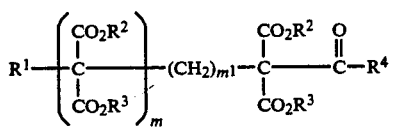

wherein:
m is an integer from 0 to 1;
$m^1$ is an integer from 0 to 4;
$R^1$ is a $C_1$-$C_{20}$ radical selected from the group consisting of alkyl, cycloalkyl, alkenyl, cycloalkenyl, phenyl, aryl, benzoyl and aroyl radicals, and when m is 0 and $m^1$ is at least 1 then $R^1$ can be hydrogen;
$R^2$ and $R^3$ are radicals selected from the group consisting of $C_1$-$C_{12}$ alkyl and $C_5$-$C_{12}$ cycloalkyl radicals; and
$R^4$ is independently selected from the same group as $R^1$ except that $R^4$ is other than hydrogen, benzoyl and aroyl radicals.

A method is also provided for removing stains from a stained substrate by contacting in an aqueous medium the substrate with a bleaching composition as defined above.

Certain novel precursor compounds are also herein reported having the structures:

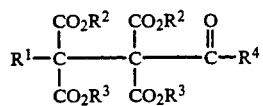

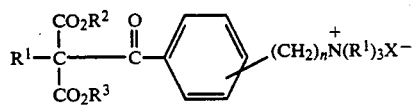

wherein
$R^1$, $R^2$, $R^3$ and $R^4$ are radicals as hereinabove defined, n is an integer from 0 to 8, and $X^-$ is an anion which assists in providing solubility to the precursor.

DETAILED DESCRIPTION

Now a group of precursor compounds having novel leaving groups have been identified that are of pleasant odor, cleaning effective and biodegradable. These precursors are malonate esters. Synthesis of these compounds is relatively facile. The compounds are achievable by reaction of acid halides with a malonate.

Illustrative of the bleach precursors of this invention are compounds having the structure:

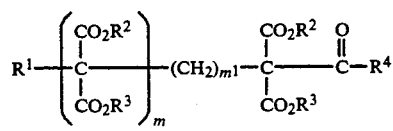

wherein:
m is an integer from 0 to 1;
$m^1$ is an integer from 0 to 4;
$R^1$ is a $C_1$-$C_{20}$ radical selected from the group consisting of alkyl, cycloalkyl, alkenyl, cycloalkenyl, phenyl, aryl, benzoyl and aroyl radicals, and when m is 0 and $m^1$ is at least 1 then $R^1$ can be hydrogen;
$R^2$ and $R^3$ are radicals selected from the group consisting of $C_1$-$C_{12}$ alkyl and $C_5$-$C_{12}$ cycloalkyl radicals; and
$R^4$ is independently selected from the same group as $R^1$ except that $R^4$ is other than hydrogen, benzoyl and aroyl radicals.

All radicals noted above may either be unsubstituted or substituted with a variety of substituents. Particularly advantageous is the presence of an electron withdrawing group on the aryl radical. Typical substituents may include alkyl, cycloalkyl, carboxylate, carboalkoxy, alkoxy, ketoxy, malonato, heterocyclic ring, polyoxyalkylene, halo, nitro, sulpho, sulphato, cyano, trifluoromethyl, hydroxy, quaternary ammonium, alkylene quaternary ammonium, haloalkyl radicals and mixtures thereof.

Precursors of this invention will normally be present in amounts ranging from about 0.1 to about 40%, preferably from about 0.5 to 5% by weight of the composition.

Illustrative of structure I is compound 1:

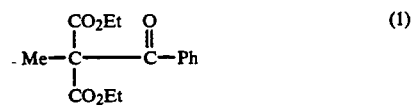

Certain novel compounds are also herein disclosed having structures II and III:

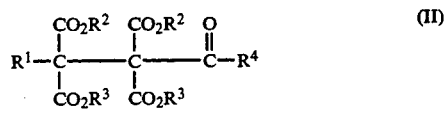

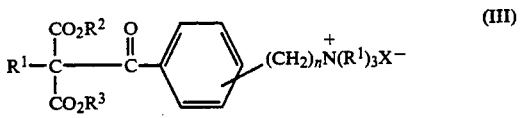

Anion $X^-$ may be selected from the group consisting of halide, hydroxide, phosphate, sulphate, methyl sulphate and acetate anions.

Specific examples of structure II are compounds 2 and 3:

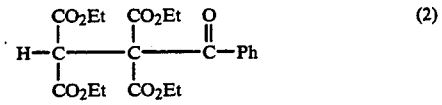

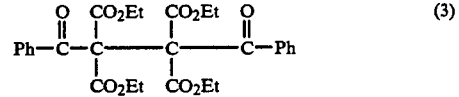

Specific examples of structure III are compounds 4 and 5.

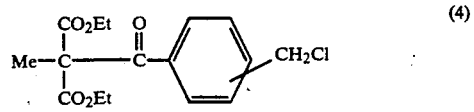

-continued

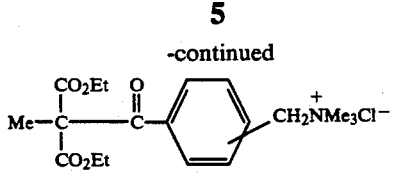 (5)

The foregoing precursors may be incorporated into detergent bleach compositions which require as an essential component a peroxygen bleaching compound capable of yielding hydroperoxyl anions in an aqueous solution.

Peroxygen compounds providing hydroperoxyl anion sources are well-known in the art. They include the alkali metal peroxides, organic peroxide bleaching compounds such as urea peroxide, and inorganic persalt bleaching compounds, such as the alkali metal perborates, percarbonates, perphosphates and persulfates. Mixtures of two or more such compounds may also be suitable. Particularly preferred are sodium perborate tetrahydrate, sodium percarbonate, and, especially, sodium perborate monohydrate. Sodium perborate monohydrate is preferred because it has excellent storage stability and dissolves very quickly in aqueous bleaching solutions.

Peroxygen compounds for use in compositions of this invention will be present in amounts ranging from about 1 to about 60%, preferably from about 5 to about 20% by weight. Typically, the ratio of hydroperoxyl anion (or a peroxygen compound generating the equivalent amount) to precursor will range from about 0.5:1 to 10:1, preferably, 1:1 to 4:1, most preferably 1:1 to less than 1.5:1.

A detergent formulation containing a bleach system consisting of an active oxygen releasing material and a novel compound of the invention will usually also contain surface-active materials, detergency builders and other known ingredients of such formulations.

The surface-active material may be a naturally derived or synthetic material selected from anionic, nonionic, amphoteric, zwitterionic, cationic actives and mixtures thereof. Many suitable actives are commercially available and are fully described in the literature, for example, in "Surface Active Agents and Detergents", Volumes I and II, by Schwartz, Perry and Berch. The total level of the surface-active material may range up to 50% by weight, preferably being from about 0.5% to 40% by weight of the composition, most preferably 4 to 25%.

Synthetic anionic surface-actives are usually water-soluble alkali metal salts of organic sulfates and sulfonates having alkyl radicals containing from about 8 to about 22 carbon atoms.

Examples of suitable synthetic anionic detergent compounds are sodium and ammonium alkyl sulfates, especially those obtained by sulfating higher ($C_8$–$C_{18}$) alcohols produced for example from tallow or coconut oil; sodium and ammonium alkyl ($C_9$–$C_{20}$) benzene sulphonates, sodium alkyl glyceryl ether sulphates, especially those ethers of the higher alcohols derived from tallow or coconut oil and synthetic alcohols derived from petroleum; sodium coconut oil fatty acid monoglyceride sulphates and sulphonates; sodium and ammonium salts of sulphuric acid esters of higher ($C_9$–$C_{18}$) fatty alcohol-alkylene oxide, particularly ethylene oxide, reaction products; the reaction products of fatty acids such as coconut fatty acids esterified with isethionic acid and neutralized with sodium hydroxide; sodium and ammonium salts of fatty acid amides of methyl taurine; alkane monosulfonates such as those derived by reacting alpha-olefins ($C_8$–$C_{20}$) with sodium bisulfite and those derived by reacting paraffins with $SO_2$ and $Cl_2$ and then hydrolyzing with a base to produce a random sulfonate; sodium and ammonium $C_7$–$C_{12}$ dialkyl sulfosuccinates; and olefin sulfonates, which term is used to describe the material made by reacting olefins, particularly $C_{10}$–$C_{20}$ alpha olefins, with $SO_3$ and then neutralizing and hydrolyzing the reaction product. The preferred anionic detergent compounds are sodium ($C_{11}$–$C_{15}$) alkylbenzene sulfonates, sodium ($C_{16}$–$C_{18}$) alkyl sulfates and sodium ($C_{16}$–$C_{18}$) alkyl ether sulfates.

Examples of suitable nonionic surface-active compounds which may be used, preferably together with the anionic surface-active compounds, include in particular the reaction products of alkylene oxides, usually ethylene oxide, with alkyl ($C_6$–$C_{18}$) phenols, generally 5–25 EO, i.e. 5–25 units of ethylene oxides per molecule, the condensation products of aliphatic ($C_8$–$C_{18}$) primary or secondary linear or branched alcohols with ethylene oxide, generally 2–30 EO, and products made by condensation of ethylene oxide with the reaction products of propylene oxide and ethylene diamine. Other so-called nonionic surface-actives include alkyl polyglycosides, long chain tertiary amine oxides, long chain tertiary phosphine oxides and dialkyl sulphoxides.

Amphoteric or zwitterionic surface-active compounds can also be used in the compositions of the invention but this is not normally desired owing to their relatively high cost. If any amphoteric or zwitterionic detergent compounds are used, it is generally in small amounts in compositions based on the much more commonly used synthetic anionic and nonionic actives.

The detergent compositions of the invention will normally also contain an additional detergency builder, as mentioned above. Builder materials may be selected from (1) calcium sequestrant materials, (2) precipitating materials, (3) calcium ion-exchange materials and (4) mixtures thereof.

In particular, the compositions of the invention may contain any one of the organic or inorganic builder materials, such as sodium or potassium tripolyphosphate, sodium or potassium pyrophosphate, sodium or potassium orthophosphate, sodium carbonate, the sodium salt of nitrilotriacetic acid, sodium citrate, carboxylmethylmalonate, carboxymethyloxysuccinate, tartrate mono- and di-succinates, oxydisuccinate, crystalline or amorphous aluminosilicates and mixtures thereof.

Polycarboxylic homo- and co-polymers may also be included as builders and to function as powder structurants or processing aids. Particularly preferred are polyacrylic acid (available under the trademark Acrysol from the Rohm and Haas Company) and acrylic-maleic acid copolymers (available under the trademark Sokalan from the BASF Corporation) and alkali metal or other salts thereof.

These builder materials may be present at a level of, for example, from 1 to 80% by weight, preferably from 10 to 60% by weight.

Upon dispersal in a wash water, the initial amount of peroxygen compound should range anywhere from about 0.05 to about 250 ppm active oxygen per liter of water, preferably between about 1 to 50 ppm. Bleach precursor may be present in the wash media in an amount from about 0.05 to 20 ppm, preferably from about 5 to about 10 ppm. Surfactant should be present in the wash water from about 0.05 to 1.0 grams per liter, preferably from 0.15 to 0.20 grams per liter. When present, the builder amount will range from about 0.1 to 3.0 grams per liter.

Apart from the components already mentioned, the detergent compositions of the invention can contain any of the conventional additives in the amounts in which such materials are normally employed in fabric washing detergent compositions. Examples of these additives include lather boosters such as alkanolamides, particularly the monoethanolamides derived from palmkernel fatty acids and coconut fatty acids, lather depressants such as alkyl phosphates and silicones, anti-redeposition agents such as sodium carboxymethylcellulose and alkyl or substituted alkyl cellulose ethers, other stabilizers such as ethylene diamine teraacetic acid, phosphonic acid derivatives (Dequest®), fabric softening agents, inorganic salts such as sodium sulphate, and, usually present in very small amounts, fluorescent agents, perfumes, enzymes such as proteases, cellulases, lipases and amylases, germicides and colorants.

The precursors of this invention in combination with a peroxygen compound may be useful for removing stains both in consumer type products and for industrial applications. Among consumer products incorporating this invention are laundry detergents, laundry bleaches, hard surface cleaners, toilet bowl cleaners, automatic dishwashing compositions and even denture cleaners. Stained consumer products benefiting from treatment with compositions of this invention may include clothes and other fabrics; household fixtures and appliances such as sinks, toilet bowls and oven ranges; tableware such as drinking glasses, dishes, cookware and utensils; and even dentures. The bleaching system of this invention may also be applied to industrial uses such as for the bleaching of wood pulp.

The system of the present invention may be delivered in a variety of product forms including powders, on sheets or other substrates, in pouches, in tablets, in aqueous liquids, or in non-aqueous liquids such as liquid nonionic detergents.

The following examples will more fully illustrate the embodiments of this invention. All parts, percentages and proportions referred to herein and in the appended claims are by weight unless otherwise illustrated.

EXAMPLE 1

Preparation of Diethyl Methyl Benzoyl Malonate (1)

Diethyl methyl malonate (1.74 g, 0.01 mole) was dissolved in dry THF (25 ml) and NaH (240 mg, 0.01 mole) was added at room temperature. After 30 minutes of stirring benzoyl chloride (1.40 g, 0.01 mole) in dry THF (5.0 ml) was added dropwise. The mixture was stirred at 50° C. overnight. Saturated aqueous solution of NH$_4$Cl (excess) was added and the mixture was extracted with diethyl ether (3×50 ml). The mixture was dried over MgSO$_4$ and distilled to give compound (1) in 85% isolated yield.

NMR (CDCl$_3$, TMS external reference): 7.40–8.10 (m,5H), 4.20 (q,4H), 1.80 (s,3H), 1.20 (t,6H).

IR (neat): 1780,1730 cm$^{-1}$.

EXAMPLE 2

Preparation of 1-Benzoyl-Tetraethyl-1,1,2,2-Ethane Tetracarboxylate (2)

Tetraethyl-1,1,2,2-ethane tetracarboxylate (3.18 g, 0.01 mole) was dissolved in dry THF (25 ml) and NaH (240 mg, 0.01 mole) was added. The mixture was stirred at 50° C. for 30 minutes and then benzoyl chloride (1.40 g, 0.01 mole) in dry THF (5 ml) was added dropwise. The mixture was stirred at 60° C. overnight. Saturated aqueous solution of NH$_4$Cl (excess) was added and the mixture was extracted with diethyl ether (3×100 ml) and dried over MgSO$_4$ Chromatography on silica (hexane:ether 3:1) gave the desired product (2) in 90% isolated yield.

NMR (CDCl$_3$, TMS external reference): 7.40–8.10 (m,5H), 4.10–4.50 (m,9H), 1.15–1.50 (m,12H).

IR (neat): 1780,1730 cm$^{-1}$.

EXAMPLE 3

Preparation of 1,2-Dibenzoyl-Tetraethyl-1,1,2,2-Ethane Tetracarboxylate (3)

The same procedure for the preparation of compound (2) was used.

NMR (CDCl$_3$, TMS external reference): 7.40–8.10 (m,10H), 1.20 (t,12H).

IR (neat): 1780,1730 cm$^{-1}$.

EXAMPLE 4

Preparation of 1-Benzoyl-(3–Chloromethyl)-Diethyl Methyl Malonate (4)

Diethyl methyl malonate (1.74 g, 0.01 mole) was dissolved in dry THF (25 ml) and NaH (240 mg, 0.01 mole) was added at room temperature. After 30 minutes, 3-chloromethylbenzoyl chloride (1.89 g, 0.01 mole) in dry THF (5 ml) was added dropwise. The mixture was stirred at 50° C. overnight. Saturated aqueous solution of NH$_4$Cl (excess) was added and the mixture was extracted with diethyl ether (3×100 ml) and dried over MgSO$_4$. Chromatography on silica (hexane:ether 4:1) gave the desired product in 89% isolated yield.

NMR (CDCl$_3$, TMS external reference) 7.35–8.10 (m,4H), 4.60 (s,2H), 4.20 (q,4H), 1.80 (s,3H), 1.20 (t,6H)

IR (neat): 1778–1730 cm$^{-1}$.

EXAMPLE 5

Preparation of 1-Benzoyl-(3-Trimethylammonio Methyl)-Diethyl Methyl Malonate Chloride Salt (5)

Compound (4) (1.00 g) was dissolved in CH$_3$CN (50 ml) and an excess of trimethylamine was bubbled through the reaction at −10° C. The mixture was stirred first at 0° C. and then at RT overnight. The product (5) was isolated (0.75 g) and characterized.

NMR (DMSO-d$_6$): 7.40–8.10 (m,4H), 4.95 (bs,2H), 4.20 (q,4H), 3.20 (s,9H), 1.80 (s,3H), 1.20 (t,6H).

EXAMPLE 6

Bleaching Performance

Stain bleaching ability of the precursors when combined with sodium perborate were evaluated on tea stained cloths. Typically, cotton test pieces (4 in.×4 in.) stained with the appropriate stain were washed in a Terg-O-Tometer in 1 liter of aqueous solution containing a given level of bleach precursor, hydrogen peroxide, buffer and detergent (phosphate Surf®).

Washes were carried out at 40° C. for 15 minutes at pH 8.0–9.0 with precursor concentration of 6.2×10$^{-4}$ M and an equivalent molar amount of hydrogen peroxide (perborate). Stain bleaching was measured reflectometrically using a Colorgard System/05 Reflectometer. Bleaching is indicated by an increase in reflectance, reported as ΔR. In general, a ΔR of one unit is perceivable in a paired comparison while ΔR of two units is perceivable monadically. In reporting the reflectance change, the change in reflectance caused by general detergency and bleaching by the excess hydrogen peroxide has been accounted for. Thus ΔR can actually be express as:

ΔR = (Reflectance of stained fabric washed with precursor/$H_2O_2$ and detergent—Reflectance of stained fabric before washing)—(Reflectance of stained fabric washed with $H_2O_2$ and detergent along—Reflectance of stained fabric before washing)

TABLE I

| Bleach Performance | |
| --- | --- |
| Precursor | ΔR |
| 1 | ≧6.0 |
| 2 | ≧6.0 |
| 3 | ≧6.0 |
| 4 | ≧6.0 |
| 5 | ≧12.0 |

Conditions:
40° C., BC-1 cloth, pH = 8.0–9.0 [precursor] = 6.2 × $10^{-4}$M, [$H_2O_2$] = 6.2 × $10^{-4}$M, detergent base = P-Surf ®.

The foregoing description and examples illustrate selected embodiments of the present invention. In light thereof, various modifications will be suggested to one skilled in the art, all of which are within the spirit and purview of this invention.

What is claimed is:

1. A bleaching composition comprising:
   (i) a peroxygen compound present in an effective amount to generate perhydroxyl anions; and
   (ii) a bleach precursor present in an effective amount to react with said perhydroxyl anions and cause bleaching, having the structure:

$$R^1 \left( \begin{array}{c} CO_2R^2 \\ | \\ -C- \\ | \\ CO_2R^3 \end{array} \right)_m (CH_2)_{m^1} - \underset{\underset{CO_2R^3}{|}}{\overset{\overset{CO_2R^2}{|}}{C}} - \overset{O}{\underset{}{\overset{\|}{C}}} - R^4$$

wherein:
   m is 0,
   $m^1$ is an integer from 0 to 4;
   $R^1$ is a $C_1$–$C_{20}$ radical selected from the group consisting of alkyl, cycloalkyl, alkenyl, cycloalkenyl, phenyl, aryl, benzoyl and aroyl radicals, and when m is 0 and $m^1$ is at least 1 then $R^1$ can be hydrogen;
   $R^2$ and $R^3$ are radicals selected from the group consisting of $C_1$–$C_{12}$ alkyl and $C_5$–$C_{12}$ cycloalkyl radicals; and
   $R^4$ is independently selected from the same group as $R^1$ except that $R^4$ is other than hydrogen, benzoyl and aroyl radicals.

2. The composition of claim 1 wherein said peroxygen compound is present in an amount from about 1 to about 60% by weight and said bleach precursor is present in an amount from about 0.1 to 40% by weight.

3. The composition according to claim 1 further comprising from about 0.5 to 50% of a surfactant selected from the group consisting of nonionic, anionic, amphoteric, zwitterionic surface-active compounds and mixtures thereof.

4. The composition according to claim 1 further comprising a detergent builder in an amount from about 1 to about 80% by weight.

5. The composition of claim 1 wherein $R^4$ is phenyl.

6. The composition according to claim 5 wherein $R^2$ and $R^3$ are selected from the group consisting of methyl and ethyl.

7. The composition of claim 1 wherein said precursor is diethyl methyl benzoyl malonate.

8. A method of removing stains from a stained substrate comprising contacting in an aqueous medium said substrate with an effective amount for bleaching of the bleaching composition of claim 1.

* * * * *